United States Patent [19]

Pao

[11] Patent Number: 4,766,896
[45] Date of Patent: Aug. 30, 1988

[54] ANTERIOR CAPSULOTOMY PROCEDURES

[76] Inventor: David S. C. Pao, 95 Highpoint Dr., Churchville, Pa. 18966

[21] Appl. No.: 83,897

[22] Filed: Aug. 6, 1987

Related U.S. Application Data

[63] Continuation of Ser. No. 822,122, Jan. 24, 1986, abandoned.

[51] Int. Cl.$^4$ .............................................. A61B 17/32
[52] U.S. Cl. ................................................... 128/305
[58] Field of Search ................... 128/305, 304; 604/22

[56] References Cited

U.S. PATENT DOCUMENTS 4,301,802 11/1981 Poler et al. .

FOREIGN PATENT DOCUMENTS 165657 12/1985 European Pat. Off. ............ 128/305
3205959 9/1983 Fed. Rep. of Germany ...... 128/305

OTHER PUBLICATIONS

*Atlas of Eye Surgery and Related Anatomy*, Frederick H. Daviddorf et al., Keller Publishing Co. (1978), pp. 29-34 and 147-166.

Primary Examiner—Michael H. Thaler
Attorney, Agent, or Firm—Woodcock Washburn Kurtz Mackiewicz & Norris

[57] ABSTRACT

Anterior capsulotomy procedures are performed by inserting a cystitome having a freely rotating stylus with blade through a relatively small initial limbal incision severing a central portion of the anterior capsule by one or more elongated incisions made entirely through the one small limbal incision including at least one elongated incision cutting the capsule along a path extending across a diametric axis through the center point of the anterior capsule and center of the initial incision.

6 Claims, 3 Drawing Sheets

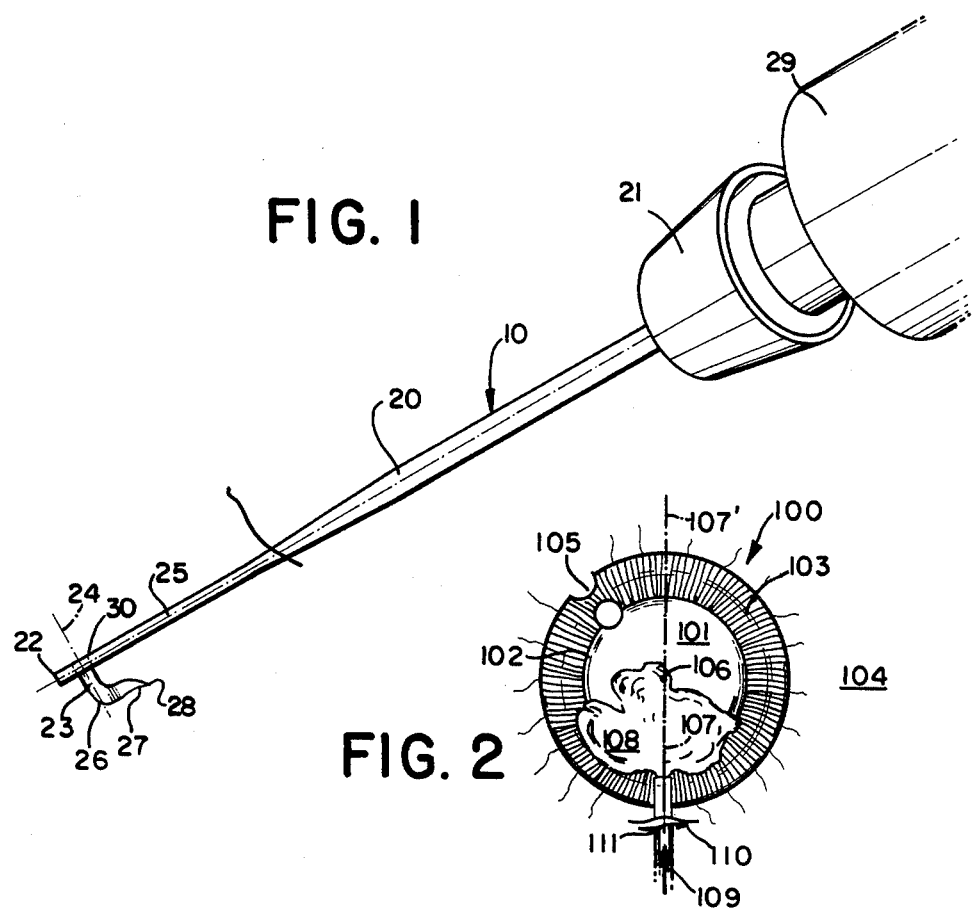
FIG. 1
FIG. 2
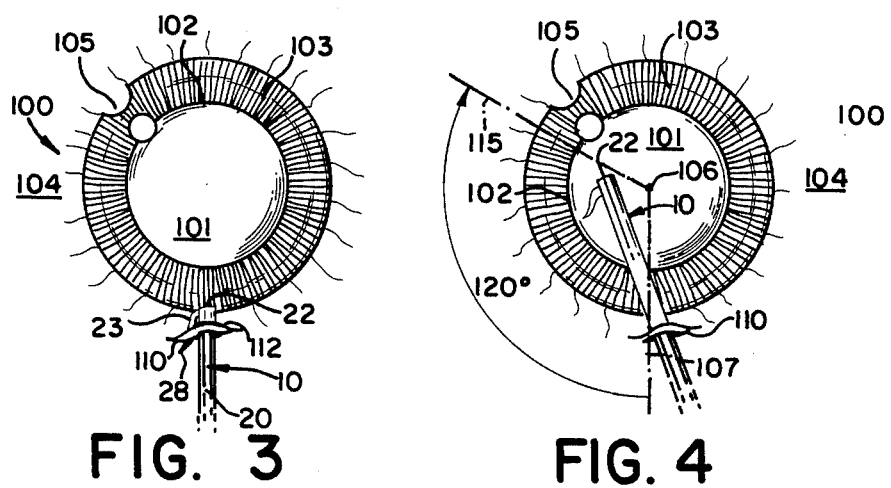
FIG. 3
FIG. 4

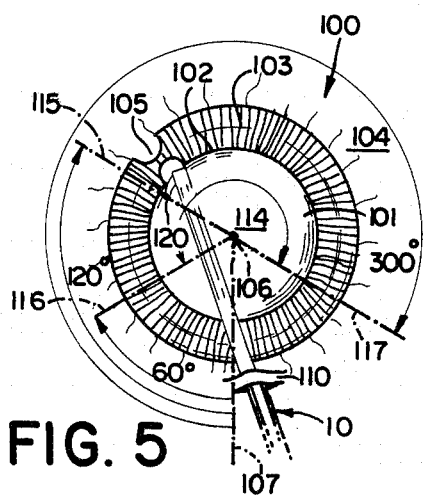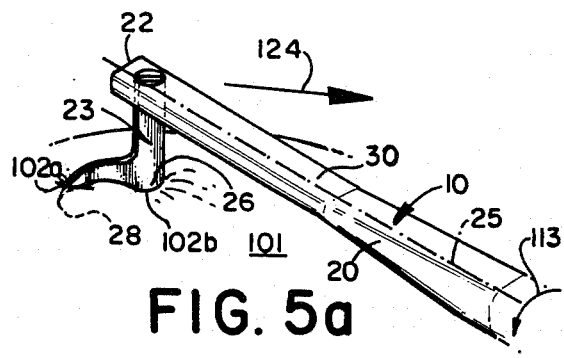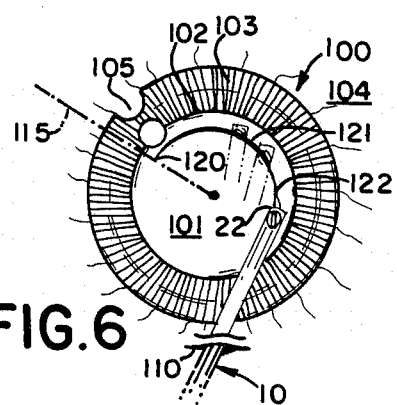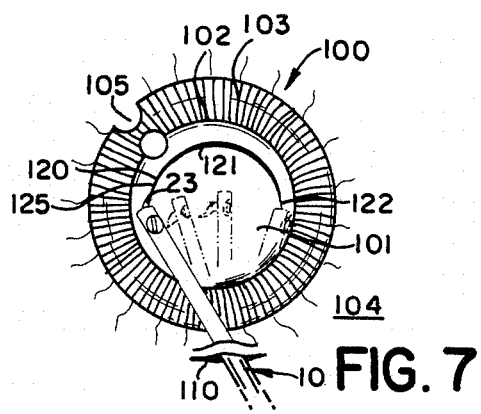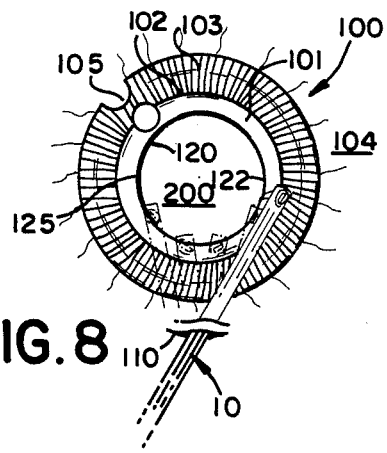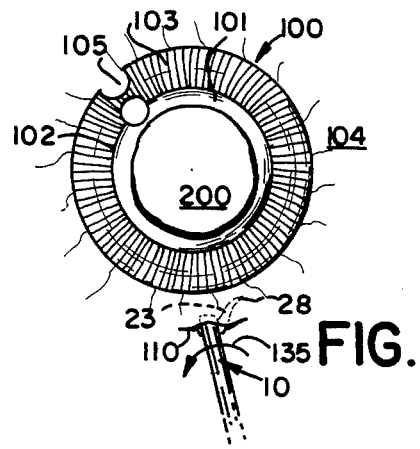

ANTERIOR CAPSULOTOMY PROCEDURES

This is a continuation of application Ser. No. 822,122, filed Jan. 24, 1986, now abandoned.

FIELD OF THE INVENTION

The invention relates to ophthalmic surgery and, in particular, to procedures for performing an anterior capsulotomy with a cystitome having a freely rotating blade.

BACKGROUND OF THE INVENTION

An anterior capsulotomy procedure is one wherein the surface of the anterior capsule of an eye is broken or partially removed allowing access to the anterior thereof. Procedures commonly performed as part of a cataract removal and other ophthalmic procedure.

The most typical anterior capsulotomy procedure performed is a "can opener technique" in which the bent tip of a 23 or 25 gauge needle inserted between the anterior capsule surface and overlying cornea is used to rip a series of small connected tears in the anterior capsule. This procedure produces flaps of anterior capsule material, called tags, which remain to obscure the surgeon's view of the capsule and to interfere with the removal of the lens and/or cortical material and the placement of an artificial lens. The tears produced by this method can also allow an implanted artificial lens to slip or escape entirely from the capsule.

At the November, 1984, Academy of Ophthalmology meeting, it was suggested that a unipolar electric probe could be used for capsule "cutting". When the probe electrode contacts the anterior capsule it permits an electric current to be passed between it and a receiving electrode contacting a patient's body elsewhere. The current coagulates the anterior capsule making it extremely friable. It was suggested that a chisel-shaped electrode could be used for simultaneously coagulating and "cutting" the coagulated capsule.

Among the significant advantages of the system was the minimization if not elimination of tags and tears. However, the proposed procedure has significant disadvantages including the possibility of producing capsule shrinkage and the rupturing of adjacent zonules from excessive heat produced by the unipolar probe. Other disadvantages include the not insignificant cost of the equipment.

There are commercially available cystitomes for such procedures providing a cutting edge with fixed orientation at the end of a handle. However, these devices also require an extremely large limbal incision or a number of smaller incisions to remove a central portion from the capsule.

SUMMARY OF THE INVENTION

It is an object of the invention to provide an improved, non-electrical procedure for performing an anterior capsulotomy.

It is yet another object to provide a procedure of performing an anterior capsulotomy on an uncoagulated eye in which a central portion of the capsule is removed.

It is yet another object to provide a procedure of performing an anterior capsulotomy on an uncoagulated capsule which minimizes shear forces and zonal stresses on the capsule, the occurrence of capsular tags and the posterior progression of capsular tears.

The above objects and others are accomplished by an anterior capsulotomy procedure comprising the steps of making a limbal incision and severing a closed curvilinear central portion of an uncoagulated anterior capsule entirely through the initial limbal incision by one or more connected elongated incisions in the anterior capsule including at least one elongated incision cutting the capsule along a path extending across a diametric axis through the center point of the anterior capsule and the center of the initial limbal incision. The advantage of using a cystitome having a rotating stylus with cutting blade is that elongated incisions can be made by cutting the capsule along one or more curved paths. This eliminates converging straight line incisions which create stress locations where the capsule is likely to tear. According to the invention, the initial limbal incision is relatively small, typically between about 1.5 and 2.0 millimeters in cord length. The freely rotating stylus of such a cystitome allows the surgeon to insert the stylus point into the anterior capsule on one side of the diametric axis and sweep the stylus traversely across the diametric axis along a curved path, if desired, allowing the severing of circular and "D" shaped curvilinear portions of the capsule. If the chord center of the limbal incision is viewed as defining a 12 o'clock (or 0°/360°) position with respect to the center point of the anterior capsule, according to the invention, one elongated incision is made across the diametric axis beginning in a sector extending from about a 2 o'clock (or 60°) position with respect to the chord center of the limbal incision, around and beyond the anterior capsule center point about a 10 o'clock (or 300°) position with respect to the limbal incision cord center. Initiating the incision in this zone assists in properly positioning of the cystitome stylus for a cutting rather than tearing action. Further according to the invention, where the one elongated incision in the anterior capsule extends less than about 180° in arc around the center of the anterior capsule, a second elongated incision is made beginning at one of the ends of the first incision. Alternatively, if the one elongated incision extends more than 180° in arc around the center of the anterior capsule, a second elongated incision is begun in the anterior capsule near but spaced from an end of the first elongated incision. This provides a connected portion of anterior capsule between incisions to maintain tension on the portion of the anterior capsule undergoing the second incision. While a substantially circular central portion of the anterior capsule can be severed, it is also possible to sever other closed curvilinear central portions of the capsule such as "D" shaped and triangular shaped sections.

These and other aspects of the invention will be apparent to one of ordinary skill in the art from the accompanying figures and following detailed description of the invention.

BRIEF DESCRIPTION OF THE DIAGRAMMATIC FIGURES

FIG. 1 is perspective view of a "pinwheel" cystitome for performing the described procedure.

FIG. 2 depicts the initial limbal incision and the separation of the anterior capsule and corneal endothelium for insertion of the stylus end of the cystitome.

FIG. 3 depicts the insertion of the stylus end of the cystitome through the initial incision.

FIG. 4 depicts the initial positioning of the stylus approximately at the 4 o'clock (or 120°) position mid periphery.

FIG. 5 depicts the rotation of the cystitome 90° about its longitudinal axis and the first insertion of the stylus into the anterior capsule.

FIG. 5a is an expanded view of part of FIG. 5 illustrating the tensioning and spaced cutting characteristics of the stylus.

FIG. 6 depicts the first incision in the anterior capsule extending less than 180° in arc around the center point of the anterior capsule.

FIG. 7 depicts the beginning of the second incision in the anterior capsule at an initial end of the first incision.

FIG. 8 depicts completion of the second incision in the anterior capsule severing a circular central portion of the anterior capsule.

FIG. 9 depicts removal of the stylus through the limbal incision.

DETAILED DESCRIPTION OF THE INVENTION

Figure 10:
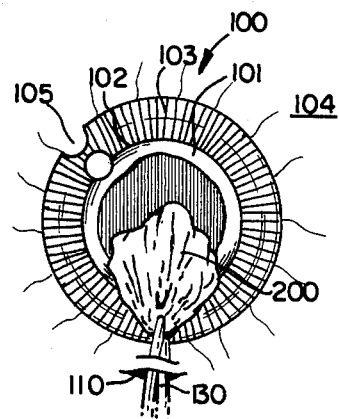
FIG. 10 depicts removal of the severed circular central portion of the anterior capsule.

FIG. 1 depicts a cystitome 10 having a rotatable stylus 23 (hereinafter sometimes referred to as a "pinwheel" cystitome). This device is being manufactured by Sharpoint, Inc. and is preferred for use in performing the following procedures. The cystitome 10 includes a cannula 20 with a handle connector end 21 and a stylus end 22 supporting the stylus 23. The stylus 23 extends traversely about 1 mm from the end 22 opposite a superior side 30 of the cystitome and is pivotally mounted in the end 22 of the instrument so as to freely rotate 360° about an axis 24 extending perpendicularly to a central longitudinal axis 25 of the cannula 20. The preferred stylus 23 has multiple curves and includes a tensioning heel 26 formed by a convex blunt edge, a blade 27 formed by a connected concave edge and a piercing point 28. Alternatively, another blade shape without a heel, such as a sickle shape, might be less advantageously employed. Either blade shape is sharpened sufficiently to slice the capsule producing a smoothly cut incision. The preferred cystitome 10 is coupled with a suitable handle 29, such as a conventional irrigating handpiece or syringe, for manipulating the cystitome and for introducing fluid into the cannula 20 primarily for irrigating the stylus 23 to assure smooth and easy rotation.

FIGS. 2-13 depict a preferred and alternative anterior capsulotomy procedures of the invention employing the cystitome 10. Depicted in each of the figures is a human eye 100 with an anterior capsule 101 exposed through the pupil 102 of an the overlying iris 103, and the sclera 104 circumferentially surrounding the iris. A transparent cornea 105 overlies the anterior capsule, pupil and iris. Also depicted is the initial limbal incision 110 made in the limbus zone where the sclera and iris meet. An incision between about 1.5 mm and 2.0 mm in chord length should be sufficient for the procedure.

As is further depicted in FIG. 2, after the limbal incision 110 is made, an irrigant 108 such as Healon$^R$ or BSS$^R$ is instilled into the anterior chamber by suitable means such as a lumen 109 to tamponade the incision and to deepen the chamber for adequate clearance between the anterior capsule and the corneal endothelium. The vertical clearance in the anterior chamber at the site of the capsulotomy should be at least 2.0 mm for a capsulotomy of between about 6.0 mm and 8.0 mm in diameter to avoid corneal endothelial damage with the cystitome 10. A radial line 107 extending from the center point 106 of the anterior capsule 101 through the cord center 111 of the initial limbal incision 110 defines a 0°/360° (or 12 o'clock) position with respect to the center point 106 of the anterior capsule. Another radial line 107' from the center point 106 in an opposite direction forms with the radial line 107 a diametric axis passing through the center 111 of the incision 110. One of ordinary skill in the art will appreciate that the reference to radially extending line 107 as defining a "12 o'clock" position is made with respect to the patient. The eye 100 is depicted in FIGS. 2-14 as it would be viewed by the surgeon while standing over the patient's head. However, the incision 110 would be located above the iris and pupil if the patient were to be standing.

Referring now to FIG. 3, the stylus end 22 of the cystitome 10 is inserted through the incision 110. The stylus 23 is rotated so that its penetrating tip 28 is the last portion of the stylus to be inserted. During insertion, the stylus 23 forms a horizontal plane with the cannula 20 substantially parallel to the plane of the incision 110. The superior incision lip 112 is lifted with forceps (not depicted) to insure adequate clearance for insertion.

Referring to FIG. 4, the stylus end 22 is positioned at an approximately 4 o'clock (or 120°) position, indicated by radial line 115, mid-periphery. As shown in FIG. 5a, the cystitome rotated 90°, as indicated by arrow 113, about its longitudinal axis 25 so that the stylus is substantially perpendicular to the underlying anterior capsule plane. The tip 28 is inserted into the anterior capsule 110 at a point 120a along the 4 o'clock/120° radial line 115, again at a point mid-periphery. This provides an optimum initial cutting angle of approximately 30° between the stylus blade 27 and the plane of the anterior capsule surface 101. The stylus 23 should be engaged in a sector 114 extending from approximately the 60° (or 2 o'clock) position indicated by line 116 around and beyond the center point 106 to an approximately 300° (or 10 o'clock) position indicated by radial line 117 because the cutting angle between the blade and capsule surface plane will be less than optimal (approximately 60°) for initial cutting if the incision is begun outside that sector 114. In making the anterior capsule incisions, it is important to keep the stylus blade 27 at least substantially perpendicular to the anterior capsule plane. If there is any significant vertical deviation, the stylus blade will not cut. The blade 27 will remain perpendicular if the superior side 30 of the stylus end 22 opposite the extending stylus 23 is kept in the surgeon's view.

FIG. 5a also depicts the tensioning of the anterior capsule 101 by the heel 26 of the stylus 23. The tip of the stylus 23 pierces the anterior capsule 101 at a first point 102a and is inserted sufficiently for the heel 26 to contact and apply a downward pressure at a point 102b adjoining and spaced from the first point 102a. In use, the heel 26 first tensions a portion of the capsule which is then cut by the trailing blade 27. Thus, point 120b will be cut by the blade 27 when the end of the instrument is moved as indicated by arrow 124. As the end 22 of the cystitome 10 is swept across the anterior capsule, for instance, in the direction indicated by arrow 124, the anterior capsule 101 is progressively tensioned at the point of contact with the heel (which will follow the path made by the end 22 of the cystitome 10) and progressively cut by the trailing blade portion 27 of the stylus 23 (also along the path) while the capsule 101 is being tensioned by the heel 26. As a lateral force is imparted to the end 22 of the cystitome to begin or maintain its lateral movement, the heel 26 simultaneously pulls on the anterior capsule 101 in the same direction (i.e., the direction of arrow 124 in FIG. 5a) further tensioning the capsule 101.

Referring to FIG. 6, the stylus end 22 of the cystitome 10 is swept in a substantially radiused arc around and beyond the center point 106 from the initial location 120 along the 120° (4 o'clock) radial line 115 across the diametric axis to a second location 122 at about 9 o'clock or 270° radial position creating a first elongated incision 121. This first incision therefore subtends less than 180° in arc around the center point 106 of the capsule 101. Between the 7 and 8 o'clock (210° and 240°) positions, the movement of the cystitome 10 is slowed or even stopped momentarily so that the trailing stylus blade will rotate and align itself with the direction of movement of the stylus end 22. If the stylus 23 does not rotate sufficiently to align the blade 27 with the direction of movement, ripping or tearing forces will develop.

As is depicted in FIG. 7, the stylus 23 is removed from the end 122 of the first incision 121 and returned to the first end 120 of the first incision at approximately the 120° (4 o'clock) position and, a second elongated incision 125 begun. As is indicated in FIG. 8, the second elongated incision 125 is also a radiused curve extending in a counter-clockwise direction between the first end passing across the diametric axis between the center point 106 and limbal incision 120 to the second end 122 of the first incision 121. The completion of this second incision severs a substantially circular center portion 200 of the anterior capsule, also depicted. The nucleus may be subluxated after the completion of the second incision using the stylus 23 and cannula 20 prior to the removal of the cystitome 10.

Should an incomplete cut of the anterior capsule 101 be suspected, the stylus is moved in a rotating direction along the path of the two capsule incision, either clockwise or counterclockwise, to form a circular trough in the anterior cortex. This usually insures complete severance of the anterior capsule center portion and reduces the likelihood of anterior capsular tags.

Referring to FIG. 9, after completion of the anterior capsulotomy, the cannula 21 is rotated 90° as indicated by arrow 135 and the distal penetrating tip 28 and stylus 23 are allowed to rotate to trail forming a horizontal plane with cannula which is withdrawn through initial incision 110.

Referring to FIG. 10 the initial limbal incision 110 is extended for the insertion of forcep 130 or other suitable means to remove the severed circular portion 200 of the anterior capsule. It is important that this severed portion 200 of the anterior capsule be visualized by the surgeon to insure complete anterior capsulotomy before proceeding to nucleus removal. If the severed anterior capsule portion 200 cannot be visualized adequately by the surgeon, irrigation solution should be instilled into the anterior chamber to improve visualization.

Figure 11:
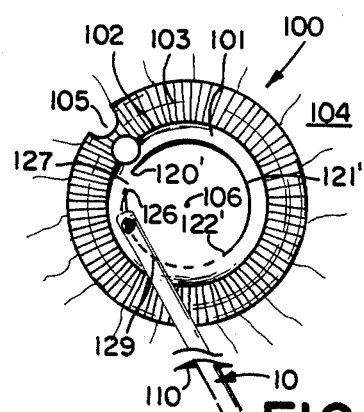
FIG. 11 depicts the completion of a second incision where a first incision has been extended more than 180° in arc around the capsule center point.

FIG. 11 depicts an alternate procedure in which a second incision is made where a first incision 121' with end locations 120' and 122' has been extended more than 180° in arc around the anterior capsule center point 106. The second incision begins at a location 126 near or adjoining the end 120' of the first incision 121' but spaced therefrom so as to maintain a bridge 127 of anterior capsule between the near end 120' of the first incision 121' and the beginning 126 of the second incision, the bridge 127 maintaining tangential tension on the anterior capsule 101 to insure smooth stylus blade engagement. The second incision is extended to the end 122' of the first incision along a path indicated by broken arc 129 passing between the center point 106 and initial limbal incision 110. The bridge 126 may then be severed by rotating the stylus along the paths of the two incisions and across the bridge in the manner previously described with respect to FIG. 8 to insure severance of the center portion of the anterior capsule.

Figure 12:
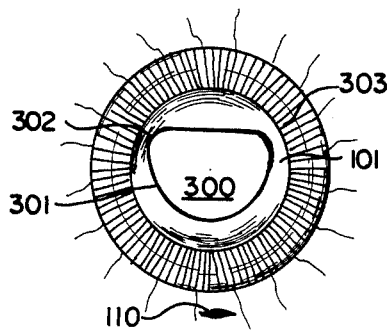
FIG. 12 depicts a suggested configuration for severing a "D" shaped central portion of the anterior capsule.
Figure 13:
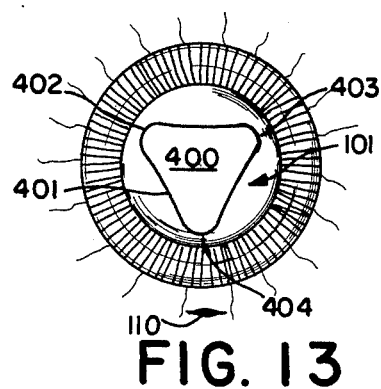
FIG. 13 depicts a suggested configuration for a triangular shaped central portion of the anterior capsule.

FIGS. 12 and 13 depict closed curvilinear incisions 301 and 401, respectively, severing a "D" shaped portion 300 and triangular portion 400, respectively, of the anterior capsule 101. The rotating stylus 14 of the described cystitome allows the stylus blade 19 to turn freely allowing cutting in all directions. The surgeon is able to "freehand" and desire pattern for the anterior capsulotomy. The D shape and triangular shape anterior capsulotomy depicted in FIGS. 11 and 12 are popular configurations allowing good visualization for in-the-bag placement of a lens implant. The described cystitome 10 allows a smooth radius of curvature at the apex points 302, 303, 402, 403 and 404. This reduces the occurrence of localized stress points generating unwanted posterior progression of the anterior capsulotomy during nucleus delivery, cordical removal and/or intraocular lens insertion.

Figure 14:
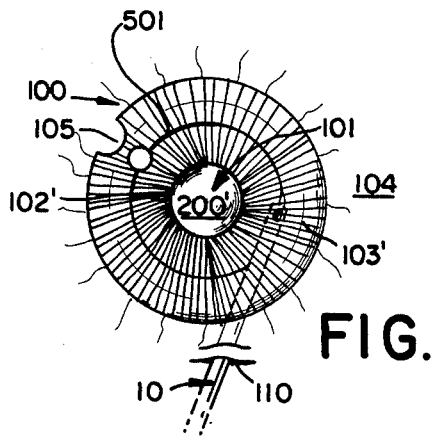
FIG. 14 depicts, diagrammatically, the severing of a central circular portion of an anterior capsule in an eye having a small pupil.

Referring to FIG. 14, where small pupils are involved, direct visualization of the incisions is not possible. The procedure in this case is performed by again making a relatively small initial limbal incision 110. An irrigant such as Healon[R] or BSS[R] is instilled to elevate the iris 103' from the underlying anterior capsule 101 sufficiently to insert the cystitome 10. One or more incisions along a path indicated by line 501 are made with the cystitome to sever a central circular portion 200' of the anterior capsule. Due to the small size of the pupil 102', these incisions will not be directly visible to the surgeon. However, many pupils will still be large enough to allow a nucleus delivery. Thus conversion to a sector iridectomy with subsequent suture closure of the pupil may not be necessary.

While the preferred embodiment of the invention has been described and variations thereto suggested, other variations will occur to the surgeon of ordinary skill and therefore my invention is not limited to the described embodiments but is defined by the scope of the accompanying claims.

I claim:

1. A method of performing an anterior capsulotomy on an eye with a cystitome having a rotating stylus comprising the steps of:
   (a) making a limbal incision in the eye;
   (b) severing a closed curvilinear central portion of an uncoagulated anterior capsule entirely through the initial limbal incision by at least two connected incisions in said anterior capsule including:

a first elongated incision slicing along a curvilinear path passing across a diametric axis of said axis of said anterior capsule from an approximately 120° position and extending less than 180° around a center point of said anterior capsule to an approximately 240° position from said initial limbal incisions, said first elongated incision slicing including a slowing of movement of said cystitome between a 210° position and a 240° position, so that said rotating stylus is permitted to rotate and align itself with a direction of said movement so as to avoid tearing said anterior capsule, and a second elongated incision slicing along a curvilinear path passing across said diametric axis from an end of said first elongated incision to the other end of said first elongated incision, said first and second elongated incisions severing the closed curvilinear central portion of said capsule.

2. The method of claim 1 wherein said second elongated incision comprises two smaller incisions wherein said first elongated incision and said two smaller incisions sever the closed curvilinear central portion of said capsule.

3. The method of claim 1 wherein said cystitome is slowed between a 210° position and a 240° position from said initial limbal incision to allow a cutting blade on the stylus to rotate and align with the direction of movement of said cystitome.

4. The method of claim 1 wherein said second elongated incision is started from the approximately 120° position.

5. The method of claim 1 wherein said rotating stylus is held substantially perpendicular to an anterior capsule incision plane.

6. The method of performing an anterior capsulotomy on an eye with a cystitome having a rotating stylus comprising the steps of:
 (a) making a limbal incision in the eye; and
 (b) severing a closed curvilinear central portion of an uncoagulated anterior capsule entirely through the initial limbal incision by at least two connected incisions in said anterior capsule including:

a first elongated incision slicing along a curvilinear path passing across a diametric axis of said anterior capsule from an approximately 120° position and extending more than 180° around a center point of said anterior capsule, and a second elongated incision slicing along a curvilinear path passing across said diametric axis from a point beginning near an end of said first elongated incision and spaced therefrom so as to maintain a bridge of anterior capsule between said end of said first elongated incision and the beginning of said second incision.

* * * * *